US008987508B2

(12) United States Patent
Maisano et al.

(10) Patent No.: US 8,987,508 B2
(45) Date of Patent: Mar. 24, 2015

(54) PROCESS FOR THE PREPARATION OF CHELATED COMPOUND

(75) Inventors: Federico Maisano, Lodi (IT); Federico Crivellin, Caselle Torinese (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 13/514,394

(22) PCT Filed: Dec. 15, 2010

(86) PCT No.: PCT/EP2010/069715
§ 371 (c)(1),
(2), (4) Date: Jun. 7, 2012

(87) PCT Pub. No.: WO2011/073236
PCT Pub. Date: Jun. 23, 2011

(65) Prior Publication Data
US 2012/0245333 A1  Sep. 27, 2012

(30) Foreign Application Priority Data
Dec. 16, 2009  (EP) ..................................... 09179438

(51) Int. Cl.
C07C 229/00 (2006.01)
C07C 229/36 (2006.01)
C07C 227/16 (2006.01)
C07C 227/40 (2006.01)

(52) U.S. Cl.
CPC ............. C07C 227/16 (2013.01); C07C 227/40 (2013.01)
USPC ........................................... 562/448; 562/442

(58) Field of Classification Search
USPC ............... 423/21.5, 7, 2; 424/9.361; 562/448, 562/470, 442; 204/82, 93
See application file for complete search history.

(56) References Cited

U.S. PATENT DOCUMENTS

| 3,172,898 | A | * | 3/1965 | Elmer | 556/148 |
| 4,711,768 | A | * | 12/1987 | Peterson et al. | 423/21.5 |
| 5,262,018 | A | * | 11/1993 | Meadow et al. | 205/470 |
| 6,162,947 | A | * | 12/2000 | Ausonio et al. | 562/448 |
| 2009/0208421 | A1 | * | 8/2009 | Meyer et al. | 424/9.361 |

FOREIGN PATENT DOCUMENTS

| EP | 0230893 | B1 | 6/1990 |
| EP | 0434345 | A1 | 6/1991 |
| SU | 138608 | A1 | 11/1960 |
| WO | 1995-032741 | A1 | 12/1995 |
| WO | 00/30688 | A2 | 6/2000 |

OTHER PUBLICATIONS

Charef Noureddine et al., Sorption Properties of the Iminodiacetate Ion Exchange Reson, Amberlite IRC-718, Towards Divalent Metal Ions, Journal of Applied Polymer Science, vol. 107, 1316-1319 (2008).*
Office Action for Russian application No. 2012129982, mail date Sep. 28, 2012 (Russian associate's English reporting of the particulars of Office Action).
First Office Action for New Zealand application No. 600910, mail date Mar. 14, 2013.
Office Action for European application No. 10790972.3, mail date May 28, 2013.
Office Action for Canadian application No. 2,784,526, mail date Oct. 11, 2013.
Office Action for Chinese application No. 201080061506.3, mail date Jan. 3, 2014 (English translation).
Lever, Susan Z. et al, "Preparation of Radioactive Lead Complexes Utilizing Chelex Methodology", Nuclear Medicine & Biology, vol. 23, 1996, pp. 1013-1017, XP004073011, ISSN: 0969-8051 Elsevier Science Inc., NY, US.
PCT International Search Report for PCT/EP2010/069715, mail date Mar. 11, 2011.
PCT Written Opinion for PCT/EP2010/069715, mail date Mar. 11, 2011.
Office Action for New Zealand application No. 600910, mail date Nov. 18, 2014.
Office Action for Russian application No. 2012129982, mail date Mar. 27, 2014 (English translation).
Office Action for Japanese application No. 2012-543706, mail date May 7, 2014 (English translation).
Office Action for Israeli application No. 220414, Jun. 25, 2014 (foreign language Office Action with associate's letter dated Jul. 9, 2014 providing translation and review of Office Action).
Office Action for New Zealand application No. 600910, mail date Jul. 1, 2014.
Decision on Grant for Patent for Russian application No. 2012129982, mail date Jul. 29, 2014 (English translation).
Office Action for Mexican application No. MX/a/2012/006954, mail date Jul. 23, 2014 (English Translation).

* cited by examiner

*Primary Examiner* — Michael G Hartley
*Assistant Examiner* — Jagadishwar Samala
(74) *Attorney, Agent, or Firm* — M. Caragh Noone

(57) ABSTRACT

The present invention generally relies on a process for the preparation of chelated compounds, comprising the selective interaction between a solid matrix and a chelating agent. In more details, the present invention enables the preparation of chelated compounds useful as diagnostic agents, in high yields and in a reliable way.

11 Claims, No Drawings

PROCESS FOR THE PREPARATION OF CHELATED COMPOUND

CROSS-REFERENCE TO RELATED APPLICATIONS

This application is the national stage application of corresponding international application number PCT/EP2010/069715 filed Dec. 15, 2010, which claims priority to and the benefit of European application no. EP09179438.8, filed Dec. 16, 2009, all of which are hereby incorporated by reference in their entirety.

The present invention relates to a process for the preparation of chelated compounds, comprising the selective ion exchange interaction between a solid support and a chelating agent. In more details, the present invention enables the preparation of chelated compounds useful as diagnostic agents.

BACKGROUND

Contrast agents (or contrast media) are a class of compounds currently employed in various medical imaging techniques to enhance the contrast of structures or fluids within the body.

From a chemical point of view, contrast agents are characterized by structural features, generally dependent on the imaging technique they are intended for. In Magnetic Resonance Imaging (MRI) and in nuclear medicine techniques, both the contrast and the therapeutic agents are usually compounds constituted by a suitable metal ion, chelated by an appropriate chelating agent, so to form a chelated compound (also indicated as paramagnetic complex). To this extent, the common procedures known in the art for the preparation of said complexes foresee the reaction of a chelating agent, usually a polyamino carboxylic acid derivative, with a given metal derivative (e.g. a paramagnetic or a lanthanide metal derivative, or even a radioisotope thereof), in a suitable medium. The chelating agent may be either purchased and used as such, or it may be functionalized or even totally synthesised, for instance, according to procedures known in the art (see among others, WO 00/30688, Bracco).

EP 0230893 discloses the preparation of a series of chelated compounds by reaction of several chelating agents with metal chlorides, in water. In spite of the good yields and reproducibility of the disclosed process the final purification steps are usually carried out in order to remove the residual salts formed during the complexation reaction.

An alternative to this procedure may be represented, for instance, by the reaction of a chelating agent with a metal oxide in lieu of the metal halide, in order to avoid the formation of the afore mentioned salts as side products, (see, for example, EP 0434345, where a paramagnetic complex is prepared by reaction of a tetraazacyclododecane derivative with $Gd_2O_3$ in an aqueous solvent system). This methodology however suffers from the problem represented by the low solubility of the starting metal oxide in the reaction medium. Therefore, particular cares have to be devoted to overcome this major issue, such as, e.g., vigorous stirring and high temperatures, with the consequent risk that product degradation or secondary unwanted reactions may occur.

Lever et al. in Nuclear Medicine & Biology, Vol. 23 pp 1013-1017 (1996) describe the labelling of a chelating drug by adsorbing radioactive lead (203 Pb) on a Chelex resin, followed by the chelation of the metal by contacting the resin with the chelating drug, i.e., dimercaptosuccinic acid (DMSA) or dibromosuccinic acid (DBSA). However, when the process is carried out using a column method a large excess of chelating agent is necessarily eluted in order to uptake the metal from the resin, with the consequence that a large amount of non-complexed acid is recovered in the final solution along with the radiolabeled complex. On the other hand, in a batch method, the described process occurred with even lower yields.

From all the above it will be apparent that there is still the need of a convenient and generally applicable way, also on industrial scale, for the preparation of chelated compounds in a pure form, in order to avoid the aforementioned drawbacks.

We have now found that when a metal of choice is adsorbed on a solid matrix and an amino carboxylic chelating agent is contacted with said loaded matrix, a corresponding metal chelated compound may be selectively formed, in high yields and in a form substantially free of side products or unreacted material, in a reliable and safe manner.

SUMMARY OF THE INVENTION

The present invention relates to a process for the preparation of a metal chelated compound or a salt thereof, comprising the steps of:
a. contacting a liquid composition containing a metal ion component with a solid support, to form a metal chelated support; and
b. contacting said metal chelated support with a liquid composition containing an amino carboxylic chelating agent or a salt thereof.

Preferred solid supports are cation exchanging solid supports, more preferably cation exchange resins, even more preferably resins functionalised with iminodiacetic functionalities.

According to a preferred embodiment of the invention, in both the above steps a) and b) the solid support is applied to a column and it is eluted with the proper liquid composition at a given flow rate, for a proper frame of time.

Preferred flow rate are constant flow rate of about 1-50 bed-volume/h, whereas, preferred column elution times are from about 30 minutes to about 3 hours.

Preferred liquid compositions are aqueous systems, more preferably water or mixture of water with organic or inorganic solvents, or even buffered aqueous systems.

The metal ion component of step a) is preferably selected from the group consisting of: inorganic salts such as halide (e.g. chloride, bromide and the like), organic salts, such as e.g. acetate and the like, either in an anhydrous or hydrate form, wherein chloride and acetate are particularly preferred.

As far as the metal ions are concerned, preferred ions are selected from the group consisting of: transition metal ions and lanthanide metal ions (i.e. ions of those metallic elements having atomic number ranging from 21 to 30, from 39 to 48, from 57 to 80 and from 89 to 103).

The metal salt solution preferably has a pH value in the range from about 3 to about 8, preferably from 4 to 6.

Once the metal has been adsorbed on the solid support according to step a), a liquid composition containing an amino carboxylic chelating agent is contacted with said support according to step b), preferably by column elution.

The chelating agent is preferably solved in the same aqueous system in which the metal ion component has been solved, whereas a preferred chelating agent is represented by an amino carboxylic compound which is able to selectively remove the metal ion adsorbed on the matrix. Particularly preferred are pentacarboxylic acid derivatives such as 4-carboxy-5,8,11-tris(carboxymethyl1)-1-phenyl-2-oxa-5,8,11-triazatridecan-13-oic acid (BOPTA) and diethylene triamine pentaacetic acid (DTPA).

According to a preferred embodiment, the solid support after step a) is subjected to a washing step, before carrying out the subsequent step b), in order to remove any trace of residual metal not supported on the solid material.

In a further preferred embodiment, the present invention relates to a process comprising the steps of:
 a. contacting a solution of gadolinium acetate in water for injection having a concentration of 10-100 mM with an iminodiacetic functionalised resin at a pH of 3-8, to form a gadolinium chelated resin; and
 b. contacting said gadolinium chelated resin with a solution of a BOPTA-meglumine salt 1:2 solution with a concentration of 0.1-0.15 M in water for injection.

DETAILED DESCRIPTION OF THE INVENTION

The present invention refers to a process for the preparation of a metal chelated compound or a salt thereof, comprising the steps of:
 a. contacting a liquid composition containing a metal ion component with a solid support, to form a metal chelated support; and
 b. contacting said metal chelated support with a liquid composition containing an amino carboxylic chelating agent or a salt thereof.

Unless otherwise provided, with the term "chelating agent" (also indicated as "chelating moiety" or "ligand" or "chelator") we intend chemical moieties, agents, compounds or molecules, either per se or in the form of a salt thereof, able to form a complex containing at least one coordinated bond with a metal.

With the terms "chelated compound", "chelated complex" or "complex" it is meant a compound consisting of a metal ion connected to a chelating agent. The expression "solid matrix" or "solid support" or "solid material" is intended to include any kind of ion exchange support, such as for instance resin, gel, polymeric materials and the like.

Thus, the term "adsorbed on" is used to indicate that the metal ion is bound to the solid support, so to constitute a metal loaded solid support.

According to a preferred embodiment of the invention, the solid support as such or eventually slurried, for example, in an aqueous medium such as water, is applied to a column, typically to a chromatographic column selected among those commonly used in organic synthesis.

Before its use, the solid support is optionally treated to remove eventual impurities that may leach from the column and collect in the eluant, by using procedures known in the art, such as, e.g., multiple water washings.

As afore mentioned, the chelated compounds of the present invention are selectively obtained by contacting a liquid composition containing the amino carboxylic chelating agent of choice, with a solid support loaded with a selected metal ion. The desired complex is typically obtained by an ion metal exchange interaction between the solid support and the chelating agent of choice.

In more details, the solid support reversibly binds a given metal ion present in a liquid medium, thereby removing or exchanging it from the liquid to which the support is contacted with. Such a contact may be realized, for instance, by mixing the solid support together with the mentioned liquid medium or, preferably, by the elution of the latter through a column containing said support.

In this direction, preferred solid supports are ion-exchange materials selected from resins, gel or polymeric materials. More preferably the solid support is a cation-exchange support, more preferably, a cation exchange resin, even more preferably a cation chelating resin.

Also preferred, are those variously functionalized cation-exchange resins, where the most preferred are resins derivatized with iminodiacetic acid or thiourea moieties.

Not limiting examples of said solid supports are, among others, Amberlite IRC 748 I (Rohm and Haas Company, Philadelphia, U.S.A.), Purolite S-930 (The Purolite Company, Bala Cynwyd, Pa., USA), Lewatit TP207 and Lewatit TP 208 (Lanxess AG, Leverkusen, Germany), Chelex 100 (Bio-Rad Laboratories, Richmond, Calif., USA), being the latter particularly preferred. The column containing the solid support is loaded according to the above mentioned step a), with the liquid medium containing the metal ion component, for example, by gravity or by modified pressure elution, or by a suitable pump, for a proper frame of time and at a monitored flow rate. These conditions should enable the resin to reversibly adsorbs the metal, typically by complexation, so to constitute a metal ion loaded solid resin.

Depending on the selected support, or on the concentration or the viscosity of the liquid composition containing the metal ion of choice, preferred elution times are from about 30 minutes to about 3 hours, whereas preferred monitored flow rate are constant flow rate of about 1-50 bed-volume/h.

Typically, the elution (or in case multiple elutions carried out by recycling the same eluted medium) through the column occurs until a desired percent of the support, e.g. about 70-100% of the theoretical capacity of the matrix, is chelated with the metal ion. The effective amount of the loaded metal can be suitably monitored by measuring the metal concentration in the eluted solution, and calculating by difference the total molar amount of the loaded metal.

The metal ion components are selected from inorganic salts such as halide (e.g. chloride, bromide and the like), and organic salt, such as e.g. acetate and the like, either in an anhydrous or hydrate form. Preferred metal ion components are acetate or chloride.

The metal ion is preferably selected from the group consisting of: transition metal ions and lanthanide metal ions (i.e. ions of those metallic elements having atomic number ranging from 21 to 30, from 39 to 48, from 57 to 80 and from 89 to 103) aluminium(III), gallium(III), indium(III), tin(II), and lead(II), whereas ions of lanthanide and transition metal are more preferred. In a further preferred embodiment of the invention, the metal ion is gadolinium(III), and the metal salt is gadolinium chloride ($GdCl_3$) or gadolinium acetate (Gd $(OAc)_3$).

As introduced above, in step a) of the present process, the solid matrix is loaded with the formerly described metal ion component, being the latter present in a liquid medium. Preferably, the metal ion component is solved in an aqueous system. Preferred systems are selected from: water, distilled water, pyrogens free water, water for injection (also indicated as WFI). The aqueous system may further comprise a polar organic solvent, such as polar organic solvents, lower ($C_1$-$C_4$) alcohols, tetrahydrofuran (THF), and the like, including mixtures thereof.

The metal salt solution should preferably have a pH value in the range of about 3-8, more preferably comprised from 4 to 6. In this respect, the solution preferably contains a buffer system or, when required, the pH may be adjusted by addition of a proper amount of a base, such as, for example, an alkaline base or the like.

The concentration of the metal ion in the aqueous solution ranges from 5 to 200 mM, preferably from 10 to 100 mM.

The solid support obtained in step a) is preferably washed with an aqueous liquid medium to remove the metal excess and, in case, some loosely bound metal ions. To this end, and to facilitate the removal of eventual traces of free metal, selected anions may also be included in this liquid medium, such as, but not limited to, anions of organic acids, e.g., acetate, propionate, succinate, citrate, etc.

After this washing step, a liquid composition containing the amino carboxylic chelating agent is contacted with the metal loaded solid support, according to the step b), preferably by percolation through the column under monitored conditions, for a period of time of about 10 to 180 min.

The chelating agent is solved in a liquid medium selected among those as defined above, for step a), so to constitute a chelating agent liquid medium. Accordingly, aqueous systems are preferred and even more preferably, the aqueous solution is the same for both the step a) and b)).

The chelating agent is represented by an amino carboxylic compound which is able to selectively remove the metal ion adsorbed on the solid material. In this direction, preferred chelating agents are either cyclic or acyclic amino carboxylic acids selected from: BOPTA (4-carboxy-5,8,11-tris(carboxymethyl1)-1-phenyl-2-oxa-5,8,11-triazatridecan-13-oic acid), DTPA (diethylene triamine pentaacetic acid), DOTA (3,6-dioxaoctane-1,8-diamine-NNN'N'-tertaacetic acid), EDTA (ethylenediamine-tetraacetic acid), HEDTA (N-hydroxyethyl-ethylenediamine triacetic acid), CDTA (1,2-cyclohexylendinitro-tetraacetic acid), NTA (nitrilotriacetic acid) and the like; whereas pentacarboxylic acid derivatives BOPTA and DTPA are the more preferred ones.

In order to increase the solubility of the chelating agent in the aqueous system, an inorganic base such as NaOH, $Na_2CO_3$ and the like, or an organic base, such as ammonia, meglumine and the like, is added to the solution, preferably in a stoichiometry ratio of 1 to 5 equivalents, with respect to the chelating agent, forming by that the corresponding chelating agent salt thereof. Preferably, the base is meglumine and the preferred molar ratio is 2:1 with respect to the chelating agent.

The concentration of the solution may be properly chosen, for example, so that an efficient and convenient elution through the column may be obtained.

The molar amount of the chelating agent in solution however should not be in excess over the metal amount actually present on the matrix, in order to avoid the elution of the chelating agent in excess together with the formed complex.

Preferred concentrations are from 50 mM to 150 mM, more preferably from 60 mM to 100 mM.

The process is suitably monitored by using analytical methods, e.g., UV-detection or thin layer chromatography (TLC) or complexometric titrations.

As extensively described above, the chelated compounds of the present invention are selectively obtained by contacting a liquid composition containing the amino carboxylic chelating agent of choice, with a solid matrix loaded with a selected metal ion, in line with the afore described steps a) and b).

Advantageously, the present process allows for the recovering of the final complex in high yields (>90%) and in a substantially pure form, i.e. basically with undetectable amounts of side products or unreacted materials, such as the free chelating agent, or the free metal.

In fact, as also indicated in the experimental part herein below, the chelated complex is collected with a content of impurities lower than 0.5%. Even further, no excess of chelating agent is needed, and the process is conveniently carried out by using water as solvent, which is a non toxic and environmentally friendly solvent.

In a representative procedure and according to a preferred embodiment, the BOPTA ligand is solved in water for injection (WFI) containing about 2 equivalents of meglumine, at room temperature, forming a BOPTA-meglumine salt 1:2 solution, with a concentration of about 0.1-0.15 M. Such solution is then eluted through a column containing the Amberlite IRC 748i resin, saturated with Gd(III) ions, at an elution rate of about 1 to 1.5 bed-volume/h. even more preferably, the present process comprises the steps of:
 a. contacting a solution of gadolinium acetate in water for injection having a concentration of 10-100 mM with an iminodiacetic functionalised resin at a pH of 3-8, to form a gadolinium chelated resin; and
 b. contacting said gadolinium chelated resin with a solution of a BOPTA-meglumine salt 1:2 solution with a concentration of 0.1-0.15 M in water for injection The desired meglumine salified Gd-BOPTA complex of Formula (I) is thus selectively obtained in high yield (>90%, purity>99.5%, misured by HPLC analysis) with undetectable amount of free ligand or other side products.

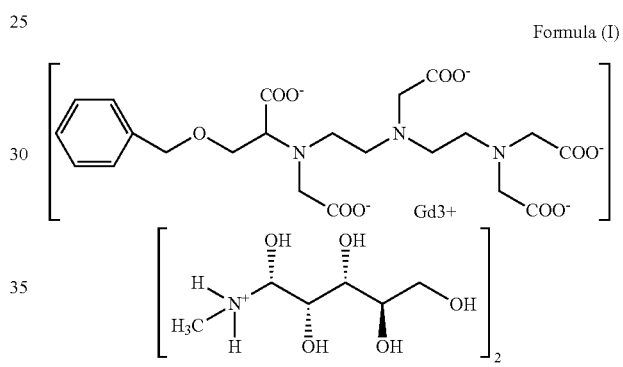

Formula (I)

The chelated agents obtained by the present process is used, for example, in the preparation of injectable formulations complying with the requirements and the guidelines demanded by the various regulatory authorities. For example, the concentration of the chelated agent solution may be adjusted to proper values by evaporation, nanofiltration or addition, for instance, of WFI (or any another proper medium) and the addition of supplementary pharmaceutical ingredients (i.e. adjuvants, stabilizers, carriers, pharmaceutical acceptable neutralizing agents and the like) may be required before submitting the composition to a final sterilization step. Likewise, this final step may be performed by procedures commonly employed in the art, for instance by high pressure saturation steam procedures.

Accordingly, the gadobenate dimeglumine solution obtained as previously described, may be used, for example, in the preparation of the commercially available contrast agent formulation, commonly known as MultiHance®.

Alternatively, the chelated compounds of the present process, is isolated in a solid form, by means of procedures known in the art, such as, for instance, solvent evaporation, liophilization, spray-drying, and the like. Said solid form may be conveniently stored or employed, for example as a part of a kit, intended for diagnostic or therapeutic purposes.

From all the above, it will be apparent that the process of the present invention, comprising the formation of a metal supported matrix (step a)) followed by an ion exchange interaction (step b)) advantageously enables the preparation of various chelated compounds, by an efficient and time saving procedure, substantially avoiding the drawbacks related to the prior-art procedures. Furthermore, the present process allows for the recovering of the final complex in high yields and in a substantially pure form, i.e. basically with undetectable amounts of side products or unreacted materials, such as the free chelating agent, or the free metal.

Noteworthy, the process of the invention may be conveniently employed for the synthesis, even on a large scale, of paramagnetic chelated compounds, intended for the use as diagnostic agents.

The following examples of the practice of the present invention are meant to be illustrative and are in no way limiting the scope of the invention.

EXPERIMENTAL PART

Example 1

Loading the Resin with Metal Ions

A 10×90 mm column was prepared with 5 g of Amberlite IRC748I (Rohm and Haas Company, Philadelphia, U.S.A.) in water. A 10-100 mM Gadolinium Acetate hydrate (325678, Aldrich) solution (minimum content 0.75 mmol Gd) was circulated through the column for 3 hours at 5 mL/min. Then, loosely bound metal ions were removed by washing the column with 30 mL of a 0.5-2 M Sodium Acetate Solution pH 6, followed by water until no more Gadolinium was in the flow through. The absence of Gadolinium was proved by dropping 100 µL of column flow through into 400 µL of Xylenol Orange solution (Xylenol Orange 0.005% in 0.2 M MES buffer pH 5.8): it should not turn violet.

Example 2

Complex Preparation—Column Procedure

A 86 mM BOPTA dimeglumine solution (7.5 mL) was loaded on the column prepared as described in Example 1 and eluted with water at flow rate 0.2 mL/min. The run was monitored for UV absorbance, pH and conductivity. 1-mL fractions were collected.

The gadobenate (UV absorbing) containing fractions were pooled together (11 mL). Gadobenate concentration was determined by HPLC analysis: 56 mM, accounting for 96% yield. No free Gd or free BOPTA were detectable by complexometric titrations.

Example 3

Complex Preparation—Batch Procedure

The resin prepared as described in Example 1 was transferred into a 15 mL polypropylene test tube, with the addition of 4 mL water and 7.5 mL of 88 mM BOPTA dimeglumine. The resin was gently shacked for 1 h at room temperature. At the end of the incubation the resin was transferred again in the column and the solution was recovered with a syringe. Water was added to the resin (2×7 mL), withdrawn with the syringe and combined with the previous Gadobenate solution. Yield: 23.5 mL of 26 mM Gadobenate, accounting for 93% yield. No free Gd or free BOPTA were detectable by complexometric titrations.

The invention claimed is:

1. A process for the preparation of a gadolinium (III) metal chelated compound or a salt thereof, comprising the steps of:
 a) contacting a liquid composition containing a gadolinium (III) metal ion component with a solid support wherein the solid support is a resin derivatized with iminodiacetic acid or thiourea functionalities, to form a metal chelated support;
 b) contacting said gadolinium (III) metal chelated support with a liquid composition containing an amino carboxylic chelating agent or a salt thereof; and
 c) recovering a gadolinium (III) metal chelated amino carboxylic agent or a salt thereof.

2. The process according to claim 1 further comprising the washing with an aqueous liquid medium of the metal chelated support of step a), before performing step b).

3. The process according to claim 1, wherein the metal ion component is a metal salt or a metal oxide.

4. The process according to claim 3, wherein the metal ion component is gadolinium acetate.

5. The process according to claim 4, for the preparation of gadobenate dimeglumine, comprising the steps of:
 a. contacting a solution of gadolinium acetate in water for injection having a concentration of 10-100 mM with an iminodiacetic functionalised resin at a pH of 3-8, to form a gadolinium chelated resin;
 b. contacting said gadolinium chelated resin with a solution of a BOPTA-meglumine salt 1:2 solution with a concentration of 0.1-0.15 M in water for injection; and
 c) recovering the gadobenate dimeglumine (Gd-BOPTA) in solution.

6. The process according to claim 1, wherein the liquid composition in step a) and in step b) is an aqueous solution.

7. The process according to claim 6, wherein the liquid composition is water for injection.

8. The process according to claim 1, wherein the pH of the metal salt solution is from 3 to 8.

9. The process according to claim 1, wherein the liquid composition containing the amino carboxylic chelating agent or a salt thereof, further comprises meglumine in a molar ratio of 2:1, with respect to the chelating agent.

10. The process according to claim 9, wherein the chelating agent is BOPTA or a pharmaceutically acceptable salt thereof.

11. The process according to claim 1, wherein the chelating agent is BOPTA or a pharmaceutical acceptable salt thereof.

* * * * *